US006982295B2

(12) United States Patent
Godwin et al.

(10) Patent No.: US 6,982,295 B2
(45) Date of Patent: Jan. 3, 2006

(54) PLASTICIZERS FROM LESS BRANCHED ALCOHOLS

(75) Inventors: Allen David Godwin, Seabrook, TX (US); Jon Edmond Randolph Stanat, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 217 days.

(21) Appl. No.: 10/462,354

(22) Filed: Jun. 16, 2003

(65) Prior Publication Data

US 2004/0254393 A1   Dec. 16, 2004

(51) Int. Cl.
- C08K 5/09 (2006.01)
- C08K 5/12 (2006.01)
- B32B 15/00 (2006.01)
- D02G 3/00 (2006.01)

(52) U.S. Cl. ........................ 524/296; 524/141; 524/295; 524/296; 524/297; 524/298; 428/379

(58) Field of Classification Search ................ 524/296, 524/298, 141, 295, 297; 428/379
See application file for complete search history.

(56) References Cited

U.S. PATENT DOCUMENTS

| | | | |
|---|---|---|---|
| 2,842,514 A | 7/1958 | Bartlett et al. ............. 260/31.6 |
| 3,956,220 A * | 5/1976 | Riem et al. .................. 524/295 |
| 4,426,542 A | 1/1984 | Barker et al. ............... 568/883 |
| 4,806,425 A | 2/1989 | Chu-Ba ....................... 428/379 |
| 5,072,057 A * | 12/1991 | Oswald et al. .............. 568/840 |
| 5,081,086 A | 1/1992 | Wilcher et al. ............... 502/81 |
| 5,189,105 A | 2/1993 | Miyazawa et al. ..... 252/182.12 |
| 5,268,514 A | 12/1993 | Bahrmann et al. .......... 568/882 |
| 5,369,162 A | 11/1994 | Bahrmann et al. .......... 524/296 |
| 5,382,716 A | 1/1995 | Bahrmann et al. .......... 568/883 |
| 5,414,160 A | 5/1995 | Sato et al. ................... 568/883 |
| 5,462,986 A | 10/1995 | Bahrmann et al. .......... 524/296 |
| 5,463,147 A | 10/1995 | Bahrmann et al. .......... 568/882 |
| 5,468,419 A | 11/1995 | Miyazawa et al. ..... 252/182.12 |
| 5,516,948 A | 5/1996 | Bahrmann et al. .......... 568/882 |
| 5,583,250 A | 12/1996 | Bahrmann et al. ............ 560/76 |
| 5,661,204 A | 8/1997 | Bahrmann et al. .......... 524/296 |
| 5,847,252 A | 12/1998 | Stine et al. .................. 585/330 |
| 5,856,604 A | 1/1999 | Stine et al. .................. 585/310 |
| 5,895,830 A | 4/1999 | Stine et al. .................. 585/259 |
| 5,990,367 A | 11/1999 | Stine et al. .................. 585/514 |
| 6,025,533 A | 2/2000 | Vora et al. ................... 585/330 |
| 6,072,093 A | 6/2000 | O'Neill et al. ............... 585/514 |
| 6,080,903 A | 6/2000 | Stine et al. .................. 585/514 |
| 6,284,938 B1 | 9/2001 | Stine et al. .................. 585/514 |
| 6,355,711 B1 | 3/2002 | Godwin et al. .............. 524/285 |
| 6,437,170 B1 | 8/2002 | Thil et al. ...................... 560/76 |
| 2005/0020718 A1 * | 1/2005 | Gosse et al. ................. 523/105 |

OTHER PUBLICATIONS

Harris et al. "The Estrogenic Activity of Phthalate Esters In Vitro", Aug97, Environmental Health Perspectives, v.105, n.8, p1-19.*

"Encyclopedia of Polymer Science and Technology", 2002, by John Wiley & Sons, Inc. Plasticizers, 5. Trimellitate Esters524.*

* cited by examiner

*Primary Examiner*—David W. Wu
*Assistant Examiner*—Mei Q. Huang
(74) *Attorney, Agent, or Firm*—Andrew B. Griffis

(57) ABSTRACT

Less branched $C_{13}$ alcohols are used to provide plasticizer esters particularly suitable for high temperature applications such as wire and cable insulation.

25 Claims, No Drawings

PLASTICIZERS FROM LESS BRANCHED ALCOHOLS

FIELD OF THE INVENTION

The invention relates to plasticizers. In an embodiment, the invention relates to less volatile plasticizers particularly suitable for use in PVC resin.

BACKGROUND OF THE INVENTION

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, poly(vinyldiene chloride), nylon, polyolefins, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in *Applied Polymer Science 21st Century*, edited by C. D. Craver and C. E. Carraher, Elsevier (2000); pp. 157–175.

Plasticizers can be characterized on the basis of their chemical structure. The most important chemical class of plasticizers are phthalic acid esters, which accounted for about 85% worldwide of PVC plasticizer usage in 2002. Two other important chemical classes are adipic acid esters, and trimellitic acid esters. Di- and tri-esters of these aforementioned acids, having a molecular weight range from about 300 to 600, typically offer a balance of solvency and compatibility with the resin, yielding plasticized materials with useful properties and good aging abilities.

Trimellitate esters are used as plasticizers in those applications where greater permanence is required. These esters are similar in structure to the phthalic acid esters, except for having a third ester functionality on the aromatic ring. Trimellitate esters provide for greater permanence primarily from reduced volatility losses but also offering reduced losses attributed to lower migration rates into other materials. Plasticized PVC electrical wire insulation prepared from either tri-2-ethylhexyl trimellitate (TOTM) or the even more permanent plasticizer triisononyl trimellitate (TINTM) will survive longer periods of high temperature service versus those products prepared from more volatile phthalate plasticizers currently available. However, the trimellitate esters are generally much more expensive, typically costing 2–3 times that of the phthalate esters such as DEHP (di-2-ethylhexyl phthalate) or DINP (diisononyl phthalate) and yield more expensive plasticized PVC electrical wire insulation. PVC formulations using trimellitate plasticizers are also more difficult to process when compared with PVC formulations that use only phthalate esters as plasticizers.

Plasticizer selection for electrical wire insulation is dependent upon the performance specifications of the insulation material and the jacketing. Performance specifications and tests such as accelerated aging tests (at various temperatures), and the like are well known in this art and are described by UL (Underwriters Laboratory) methods, e.g., UL 83. For example, for those products designed for extended periods of use at 90° C. or 105° C., often evaluated in accelerated aging studies for seven (7) days at 136° C., will contain primarily the more costly trimellitate plasticizers. A typical formulation for this 90° C. or 105° C. rated product is shown in Table 1, column A. (European designations are different from those used in the United States. For instance, 105° C. designations according to VDE Specification Code 0207 are YI 8 and YM 4).

On the other hand, flexible PVC insulation designed for extended periods of use at 60° C., characterized by accelerated oven aging testing at 80° C. or 100° C., can be prepared from less costly plasticizers such as DINP or DEHP. A typical formulation for this 60° C. rated product is shown in Table 1, column B.

Flexible PVC compounds prepared with trimellitate esters such as TOTM or TINTM generally exceed the minimum retained properties after aging specification for 90° C. or 105° C. electrified wire insulation compounds, such as those required to meet the 105° C. Class 12 (UL62), 105° C. Appliance (UL758), NM-B 90° C. building wire (Romex®, non-metallic sheathed cable, PVC jacket), or THHN 90° C. building wire (thermoplastic PVC insulation, high heat resistant, 90° C. rating, dry or damp, nylon jacket), while those products prepared with only the lower cost phthalate esters fail.

However, it is a common practice to partially substitute some of the expensive trimellitate esters with less expensive, higher molecular weight phthalate esters. As the concentration of phthalate ester in the plasticizer system increases, performance in the accelerated aging test will decrease, but there is enough flexibility in this formulating to offer a measurable cost savings while still meeting the product performance requirements.

An example of this use of triimellitate plasticizer blended with a heavier molecular plasticizer is the formulation described by L. G. Krauskopf, *Handbook of PVC Formulations*," edited by E. J. Wickson, "Monomeric Plasticizers," 1993, John Wiley & Sons, page 201, which describes for UL method 83 THHN applications, an insulation material prepared using the formulation shown in Table 1, column C. "UDP" is undecyl dodecyl phthalate (Jayflex™ UDP, available commercially, as are all Jayflex™ plasticizers cited herein, from ExxonMobil Chemical Company, Baytown, Tex.). The stabilizer used is Dythal™ lead stabilizer, available commercially as a phthalate or sulfate salt. According to this reference, the formulation exhibited 72% retained elongation after aging for seven (7) days at 136° C., exceeding the minimum specification of 65% retained elongation.

TABLE 1

| A | B | C |
|---|---|---|
| 100 kg PVC resin | 100 kg PVC | 100 kg PVC |
| 45 kg TOTM | | 25 kg TINTM |
| | 60 kg DINP | 25 kg UDP |
| 30 kg CaCO$_3$ or clay | 50 kg calcium carbonate | 12 kg calcined clay |
| 6 kg lead stabilizer | 5 kg lead stabilizer | 6 kg lead stabilizer |
| 6 kg antimony trioxide | 6 kg antimony trioxide | 6 kg antimony trioxide |
| 0.25 kg stearic acid | 0.25 kg stearic acid | 0.2 kg stearic acid |

Other phthalates commonly blended with trimellitate esters to reduce costs while exceeding specification are diundecyl phthalate (DUP, available commercially as Jayflex™ L11P), and ditridecyl phthalate (DTDP, available commercially as Jayflex™ DTDP).

The blending of phthalate esters with trimellitate esters to make PVC insulation or jacketing PVC compounds also contributes to improved processability by reducing the melt viscosity of the flexible PVC compound. In the preparations of PVC compounds for high temperature applications, it is preferable to use as much phthalate ester as possible in the plasticizer mixture, to help reduce costs and improve processability.

However, because of the higher volatility of the phthalate esters, there are practical limitations in the type and level of phthalate esters which cannot be exceeded, for at higher phthalate levels the products begin to fail the retained tensile properties listed in the various specifications. For example, current blends of TOTM with DUP are limited to about 40 wt. % DUP as the maximum because at higher levels, product failures start to occur in retained elongation and retained tensile properties after accelerated aging, resulting in a brittle product. For this reason it is common to find commercial products with only 20 wt. % to 40 wt. % DUP in blends with TOTM to avoid product failures. As Jayflex™ DTDP has slightly lower volatility than DUP, it can be used in higher concentrations. However, it is still limited to about a 60 wt. % concentration in blends with the heavier molecular weight TINTM plasticizer, with more typical concentrations being around 50 wt. % DTDP in TINTM.

In addition to the aforementioned problems, there is also a need for alternative plasticisers to avoid problems with migration out of the plasticized material. Phthalate esters with reduced volatility facilitate their usage at higher concentrations in trimellitate blends, yielding additional cost savings and improvements in processability while still exceeding the performance specifications in the accelerated aging testings.

Important properties of a plasticizer include without limitation high plasticizing efficiency, excellent compatibility with the resin, excellent processability, excellent oxidative stability, and low volatility. Usually, when changes are made to improve one of these properties, some other important property is adversely affected. For example, an increase in alcohol molecular weight tends to reduce volatility at the expense of plasticizing efficiency. In addition, as the molecular weight of the phthalate or trimellitate ester plasticizer increases, its compatability with PVC decreases, eventually resulting in a less desirable flexible PVC product with limited potential.

The range of alcohols useful in esterification for plasticizers is generally limited from about $C_4$ to about $C_{13}$ monohydridic alcohols. It is known that the specific alcohols from which the esters are made influences the performance properties, e.g., the size and structure of the alkyl group helps determine the volatility and gellation temperature of the plasticisers and is therefore chosen according to the application in which the plasticized polyvinyl chloride is to be used. The alcohols from which the plasticisers esters are made are generally obtained by either olefin oligomerization followed by hydroformylation or by hydroformylation of olefins to form aldehydes followed by aldehyde dimerization, generally by an aldol reaction. The alkyl groups of the esters therefore vary in size and structure according to the process used to produce the alcohols.

U.S. Pat. No. 2,842,514 describes using alcohol mixtures obtained by the reaction of aldehydes obtained by the "Oxo" process, wherein an olefin feed is oxonated with carbon monoxide and hydrogen at elevated temperature and pressure in the presence of a cobalt catalyst. Particularly effective plasticizers are said to derive from certain polyhydric alcohols derived from the Oxo process esterified with $C_5$–$C_7$ saturated aliphatic acids.

U.S. Pat. No. 4,426,542 describes a process in which mixed butenes are converted to a $C_{10}$ plasticizer alcohol comprised of at least about 80–90% 2-propyl-heptanol by an oxo reaction. It is taught, for instance, that 2-propylheptanol is a well-suited plasticizer alcohol whereas 2-propyl-4-methyl-hexanol has much poorer properties. This patent teaches to moderate the temperature in the hydroformylation reaction to achieve a higher ratio of normal versus branched product, the former being more desirable.

U.S. Pat. No. 4,806,425 describes the use of electrical wiring products based on dialkyl phthalate esters having at least 11 carbon atoms in the alkyl groups and having a "higher than normal amount of antioxidant." Adding more antioxidant is not a preferred solution to the problem of getting higher phthalate blends because increased antioxidant can lead to decreases in volume resistively and can cause problems with color stability.

U.S. Pat. Nos. 5,189,105 and 5,468,419 are directed to obtaining a $C_9$ plasticizer alcohols with good cold resistance and electrical insulating properties, obtained by hydroformylating octenes derived from butene dimerization. The desired product is generally obtained by taking selected portions of the alcohol mixture obtained after conventional hydroformylation.

U.S. Pat. Nos. 5,268,514; 5,369,162; 5,382,716; 5,462,986; and 5,463,147 describe mixtures of isomeric decyl alcohols obtained by hydroformylation of 1- and 2-butene containing mixtures to obtained linear or "slightly branched chain alcohols." Phthalate esters obtained using these decyl alcohols are taught to be useful in PVC compositions, having particularly good "cold resistance."

U.S. Pat. No. 5,414,160 is concerned with an organonickel catalyst system capable of improving the yield and selectivity of octenes having a low degree of branching. The average degree of branching of the octenes is from 0.85 to 1.15. Plasticizer $C_9$ alcohols are obtained after hydroformylation of the thus-described octenes.

U.S. Pat. Nos. 5,516,948; 5,583,250; and 5,661,204 describe mixture of isomeric decyl alcohols obtained by oligomerization of propylene in the presence of deactivated zeolites as catalyst, followed by separation of the $C_9$ olefins from the oligomer mixture, then hydroformylation of the $C_9$ olefins to $C_{10}$ aldehydes, followed by hydrogenation to the corresponding alcohols. The mixtures are esterified with phthalic acid or anhydride. The alcohol product claimed in the U.S. '250 patent is at least 80% linear.

U.S. Pat. No. 6,355,711 describe a plasticizer ester prepared by esterifying an acid or anhydride with $C_7$–$C_{11}$ oxo alcohols prepared by hydroformylating $C_6$–$C_{10}$ olefins having at least 50% methyl branching at the beta carbon. Examples of this invention are $C_9$ phthalate esters obtained from the $C_9$ alcohol produced by the hydroformylation of 2-methyl heptene-1 or 2-methyl heptene-2. They are described by the patent as being useful particularly in the manufacture of PVC automotive interior trim applications, and in electrical wire jacketing compounds, however, the plasticizers discussed are too volatile for certain high-temperature applications, e.g., high temperature electrical wiring.

U.S. Pat. No. 6,437,170 relates to a mixture of isomeric nonanol diesters of adipic or phthalic acid, wherein the alcohol component of the diesters are formed from an isomeric nonanol mixture. The composition is characterized by a specific ratio of methylene and methylidene groups to methyl groups in the isononyl radical, as measured by $^1$H NMR spectra, obtainable preferably by butene dimerization using a nickel oxide catalyst followed by hydroformylation.

It is known that as the linearity of the alcohol used to make the phthalate ester increases, certain predictable events occur. One may expect reduced plasticizer volatility, improved plasticizer efficiency towards making PVC flexible, improved low temperature and flexibility, and sometimes improved processability, the latter characteristic being often a combination of plasticizer solvency and plasticizer viscosity. However, as the linearity of a plasticizer increases, its compatibility with PVC decreases, where "compatibility" is used to reference a usable product with no or slight exudation under stress. For phthalate esters based on $C_{13}$ alcohols heretofore available, compatibility with PVC is thought to decrease as the linearity increase. One reference, Alan S. Wilson, *Plasticisers*, University Press (1995), p. 137 (FIG. 4.6), indicates that for a branching index of less than 20 (20% of the total carbons are branching carbons), phthalate esters based on $C_{13}$ alcohols exhibit poor compatibility and poor processability. Commercially available phthalate esters such as Jayflex™ DTDP plasticizers are typically derived using a $C_{12}$ olefin obtained from a SPA (solid phosphoric acid) unit, followed by hydroformylation in the Oxo process. Jayflex™ DTDP has an average of 3.2 branches per alcohol moiety and a branching index of about 25 (assuming all methyl branches and calculated using the average carbon number of 12.7; some ethyl branches are present). SPA units, also known as polygas units, are well-known in the art, as discussed for instance in U.S. Pat. Nos. 6,284,938; 6,080,903; 6,072,093; 6,025,533; 5,990,367; 5,895,830; 5,856,604; 5,847,252; and 5,081,086.

The present inventor has surprisingly discovered, however, that plasticizers based on esters having, as the alcohol moiety, less branched $C_{13}$ alcohols provide for at least one of the properties of improved plasticized resin compatibility, improved processability of the resin/plasticizer mixture, lower volatility, and improved aged performance characteristics in articles formed therefrom without significantly effecting the other important properties of the plasticizer, and/or plasticizer/resin mixture, and/or final product.

SUMMARY OF THE INVENTION

The invention is directed to plasticizers based on less-branched alcohols, having certain improvements particularly when incorporated into PVC resin. The plasticizers according to the present invention are especially useful when incorporated into resins used in high temperature applications such as wire and cable insulation.

The plasticizers according to the invention are based on esters having as the alcohol moiety less branched $C_{13}$ alcohols. Less branched alcohols are defined herein as alcohols having an average branchiness of at most 2.3. This means that on average there are no more than 2.3 branches per alcohol molecule. Thus, the molecule (1):

(1)

is a $C_{13}$ alcohol having a branchiness of 1, whereas the molecule (2):

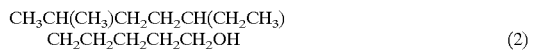
(2)

is a $C_{13}$ alcohol having a branchiness of 2; the average branchiness of a mixture containing 50% of (1) and 50% of (2) is 1.5 (percentages based on number of alcohol molecules in the mixture). In a preferred embodiment, the $C_{13}$ alcohols have an average of from 0.5 to 2.0 branches per molecule, more preferably 0.8 to 1.5. It is preferred that in any of the foregoing embodiments the branches are only methyl and ethyl branches or are only methyl branches. The structures of (1) and (2) are not intended to be limiting, particularly with regard to location of the branches or of the —OH moiety on the chain, but rather are merely illustrative of the definition of branchiness as used according to the present invention.

In a preferred embodiment wherein the branches are only methyl and ethyl branches, the branching index is preferably no more than about no more than 23 (being an average of one ethyl and methyl branch per $C_{13}$ alcohol molecule), even more preferably less than 20, and yet still more preferably about 17 (being an average of only methyl branches and an average of 2.3 branches per alcohol molecule). In an even more preferred embodiment, the limitations concerning branchiness and branching index are combined so that, for instance, an embodiment of the invention is a less branched $C_{13}$ alcohol having an average branchiness of at most 2.3 and a branching index of no more than about 30. Another embodiment is a less branched $C_{13}$ alcohol having an average branchiness of at most 2.3 and a branching index of no more than 23, even more preferably less than 20, and yet still more preferably about 17. Another embodiment is a less branched $C_{13}$ alcohol having an average branchiness of from 0.5 to 2.0 branches with the preferable, more preferable, even more preferable and yet still more preferable limitations to branching index set forth above. Yet another embodiment is the more preferable of branchiness of between 0.8 and 1.5 with the preferable, more preferable and even more preferable and yet still more preferable limitations to branching index set forth above.

In an embodiment the plasticizers are based on mixtures of trimellitate esters with ditridecyl phthalate plasticizers prepared by the reaction of less branched $C_{13}$ alcohols prepared by the hydroformylation of less branched $C_{12}$ olefins subsequently esterified with phthalic anhydride. In accordance with the definition of "less branched alcohols" above, these less branched $C_{12}$ olefins also have an average branchiness of at most 2.3.

The invention is also directed to plasticizing esters based on $C_{13}$ alcohols wherein the $^1$H or proton NMR spectrum, measured in the solvent $CDC_{13}$, the ratio of integrated area of the resonance signals with chemical shifts in the range of from 1.1 to 3.0 ppm, relative to the internal standard TMS (tetramethyl silane), to the integrated area of the resonance signals with chemical shifts in the range of 0.5 to 1.1 ppm, relative to the internal standard TMS, is about 1.20 to 3.50.

The invention is also directed to mixtures of such $C_{13}$ esters with other plasticizers, for example and without limitation, less branched $C_{12}$ and $C_{11}$ esters. In another embodiment, the invention is directed to compositions comprising a resin, such as PVC, and the $C_{13}$-based plasticizer, with or without additional plasticizers.

The invention is also directed to plasticized PVC compositions having low amounts of antioxidant therein.

Yet another embodiment of the invention includes articles comprising the aforementioned compositions, particularly insulated wire and cable.

Thus it is an object of the invention to prepare a plasticizing ester having less branching on the alcohol moiety than that provided by prior art, in order to decrease the volatility of the plasticizer in the plastic material.

Another object of the invention is to set forth a plasticizing ester prepared from a tridecyl alcohol moiety more compatible with PVC than heretofore commercially available tridecyl alcohol-based plasticizers.

Yet another object of the invention is to provide an effective substitute for more expensive plasticizers, such as trimellitates.

These and other objects, features, and advantages will become apparent as reference is made to the following detailed description, preferred embodiments, examples, and appended claims.

DETAILED DESCRIPTION

According to the invention, an ester prepared from a less branched $C_{13}$ alcohol surprisingly offers one or more of the advantages of: reduced or lower volatility, lower viscosity, and improved efficiency as a plasticizer. When used as a resin plasticizer, such as with PVC, it is more permanent, processes more easily and quickly, and is lower in cost than the trimellitate esters. The lower volatility allows for blending at higher phthalate ratios while still passing the performance requirements. This allows for less of the higher cost plasticizers, such as the trimellitates, to be used in blends. Moreover, it is particularly useful in high temperature applications such as wire and cable insulation, automotive wire, and appliance wire. In addition, less branching allows for less antioxidant in the final product, and improved flexibility at lower temperatures.

While the alcohol according to the invention may be esterified with numerous acids and acid anhydrides, such as trimellitic and adipic acids or anhydrides, it is particularly useful esterified with phthalic acid and/or phthalic anhydride to make less-branched ditridecyl phthalate (DTDP). In an embodiment, these less branched, lower volatile DTDP plasticizers are prepared through hydroformylation of corresponding less branched $C_{12}$ olefins. In yet a more preferred embodiment, the less branched $C_{12}$ olefins are made by oligomerization of butenes and propylene over surface deactivated zeolites, as described in more detail below.

In an embodiment, the plasticizing esters according to the present invention are based on a mixture of alcohols comprising less branched $C_{11}$–$C_{13}$ alcohols. These plasticizing esters derive from the esterification of acids and/or acid anhydrides with alcohols having a low amount of branching.

The alcohols according to the present invention are preferably derived from the well-known "Oxo" process, wherein compounds containing olefinic unsaturation (hereinafter "olefinic material") are contacted with synthesis gas in the presence of a hydroformylation catalyst, resulting in the formation of a product comprising an aldehyde which has one more carbon atom in its molecular structure than the starting olefinic material. Subsequent hydrogenation and separation (by, for instance, distillation) yields the desired alcohol. Thus, for instance, a feedstream comprising a $C_{12}$-containing olefinic material will produce a product comprising a $C_{13}$ alcohol. The prior art is replete with descriptions of the Oxo process per se, as mentioned above. See, for instance, U.S. Pat. Nos., 4,625,067; 5,059,718; and 6,015,928.

In a preferred embodiment, the plasticizer is comprised of a ester wherein in the $^1$H NMR spectrum, measured in the solvent $CDC_{13}$, the ratio of integrated area of the resonance signals with chemical shifts in the range from 1.1 to 3.0 ppm to the integrated area of the resonance signals with chemical shifts in the range of 0.5 to 1.1 ppm, wherein the chemical shift in ppm is measured relative to the internal standard TMS, is between 1.20 and 3.50. In a more preferred embodiment this aforementioned ratio is from about 2.40 to about 3.50. It has been found that at higher ratios, the processability improves, the volatility decreases, and the flexibility at law temperature improves. The NMR techniques are standard analytical procedures, such as described in High Resolution NMR Techniques in Organic Chemistry by Timothy D. W. Claridge, Pergamon Press, December 1999, and also in the aforementioned U.S. Pat. No. 6,437,170.

When analyzed by 1H NMR, Jayflex™ DTDP, a branched phthalate, gives a ratio of integrated areas, of 1.08. Less branched $C_{13}$ tridecyl phthalate plasticizers of this invention give an $^1$H NMR integrated area ratio of about 2.53.

The plasticizer Jayflex™ DTDP is produced by the esterification of phthalic anhydride with a branched $C_{13}$ alcohol. This alcohol also contains lesser amounts of $C_{12}$ and $C_{11}$ alcohols and is produced by the hydroformylation via the Oxo process from "tetramer," a generic name given to the predominately $C_{12}$ olefinic material obtained by oligimerization of $C_3$ or $C_4$ olefins in a SPA unit (described above). This alcohol can be characterized by $^1$H NMR and by $^{13}$C NMR as shown in Table 2 below. Table 2 is a comparison of a prior art tridecyl alcohol with a preferred tridecyl alcohol according to the present invention, as described in more detail below.

According to a preferred embodiment of the present invention, the feedstream to the hydroformylation process is an olefinic material comprising $C_{12}$ olefins which themselves are less branched alcohols. It is especially preferable that the feedstream comprise $C_{12}$ olefins are less branched alcohols and wherein the branching is short chained, e.g., one or two carbons. These may be, for instance, methyundecenes, dimethyldecenes, trimethylnonenes, ethyldecenes, methylethylnonenes. An average branchiness of at most 2.3, more preferably 0.5 to 2.0, more preferably 0.8 to 1.5 is more preferred, where the branch number refers to the average number of branches per alcohol molecule, as defined previously.

The aforementioned olefins useful in obtaining the alcohols according to the present invention may be obtained by various oligomerization processes, provided that the aforementioned average branchiness is met. In some cases fractionation to provide the appropriate cut of starting material may be necessary, which can be achieved by one of ordinary skill in the art in possession of the present disclosure.

Some of these processes produce a mixture of olefins depending on the starting material and conditions. This is sufficient for the present invention, even advantageous from a cost standpoint, provided at least some less branched $C_{12}$ is present in the mixture so that upon hydroformylation and hydrogenation a less branched $C_{13}$ is obtained.

Still more preferably the olefinic material is the olefinic reaction product of the oligomerization of various olefins using surface deactivated zeolite catalysts as described in U.S. Pat. Nos. 3,960,978; 4,021,502; 4,076,842; 4,150,062; 4,211,640; 4,520,221; 4,522,929; 4,524,232; 4,547,613; 4,568,786; 4,855,527; 4,870,038; 5,026,933; 5,112,519; 5,245,072; 5,417,869; 5,985,804; and 6,013,851.

In this most preferred embodiment, the $C_{12}$-containing olefinic material used as a feedstream in the hydroformylation reaction is prepared by contacting lower olefins under polymerization conditions with siliceous monodimensional acidic zeolites such as ZSM-22 and ZSM-23 zeolite having pore activity and wherein the zeolite surface is rendered substantially inactive for acidic reactions ("selectivated").

The zeolite may be selectivated by treatment with an amine, especially a bulky amine, i.e., one having an effective cross-section greater than that of the zeolite port size. Examples are dialkyl or more preferably trialkylpyridines. A particularly preferred amine is 2,4,6-trimethylpyridine (collidine). Alternatively a surface layer may be deposited, as described in U.S. Pat. No. 6,013,851.

By "lower olefins" or "lower olefinic material" as used herein is simply meant that the starting material to be oligomerized over the zeolite have less carbon numbers than the final product. The oligomers may be, for instance, dimers of hexenes, trimers of butenes, tetramers of propylene, or they may derive from ethylene.

The product of this preferred oligomerization product will preferably have at least 95 wt. % and more preferably 99 wt. % mono-olefin oligomers with an average of from 0.8 to 2.0, more preferably 0.8 to 1.3, methyl branches per carbon chain. In one preferred embodiment of the invention the plasticizing ester comprises a $C_{13}$ alcohol moiety containing no branching other than methyl groups.

It is preferred that the starting material for the preferred oligomerization process is a $C_3$ or greater olefin (or mixtures thereof), and in a preferred embodiment the olefinic material supplied to the oxonation reactor(s) according to the present invention derive from the oligomerization of $C_3$ and/or $C_4$ olefins using the aforementioned modified zeolites. In a particularly preferred embodiment, a feed is used comprising butenes (still more preferably n-butene) and propylene in the ratio of about 1:0.01 to 1:0.049 wt. %, yet still more preferably along with paraffins to act as a heat sink in the reaction. The amount of paraffins to use can be determined by one of ordinary skill in the art.

Another more preferred feed comprises 0.1–20 wt. % isoolefin, particularly isobutylene and or isoamylene, more preferably wherein the content of the isobutylene and/or isoamylene is from 0.5–5.0 wt. %. A preferred source of such a feed is the unreacted effluent from an MTBE unit, which is a yet still more preferable embodiment.

Yet still another preferred embodiment is the use of LAOs and/or LIOs (linear alpha olefins and linear internal olefins, respectively), which terms are well-known in the art, as olefinic feed.

Other more preferred olefinic materials used as a feed into the oxonation reactors include oligomers produced by the Octol™ process or the Dimersol™ process. See, for instance, U.S. Pat. No. 6,015,928. Other process may be used to produce the preferred olefinic starting material, such as by using oligomers produced using solid phosphoric acid (SPA) catalysts and those produced using ZSM-57 catalysts, however additional steps may be necessary to achieve the preferred material, such as fractionation.

Reactor conditions for oligomerization to obtain the feedstream for hydroformylation, for the hydroformylation reaction itself, and for subsequent hydrogenation to the desired alcohols are per se well-known in the art and are not critical to achieve the objects of the present invention.

It is important to recognize that at least some of the objects of the present invention can be achieved by an alcoholic mixture comprising $C_{13}$ alcohols but also including other alcohols, particularly $C_{12}$ and lower carbon number alcohols. Thus the olefinic material in the hydroformylation reaction may also be a mixture of $C_{12}$ olefins along with $C_{11}$ and lower carbon number olefins.

A comparison of NMR characteristics of commercially available Exxal™ 13 alcohol, produced by hydroformylating "tetramer" (oligomers of propylene produced in a SPA unit) and $C_{13}$ alcohols according to the present invention (Composition B in the Examples below) is shown in Table 2, below:

TABLE 2

Comparison of $C_{13}$ alcohols

| Product | Exxal ™ 13 alcohol | Less branched $C_{13}$ alcohol |
|---|---|---|
| Tetramer branches per molecule $^1$H NMR Results for alcohol | 3.24 | 1.28 |
| Average Carbon number | 12.4 | 13 |
| Average branches per molecule $^{13}$C NMR Results for alcohol First branch position (% of molecules) | 3.0 | 1.39 |
| C2 | 11 | 15.0 |
| C3 | 25 | 22 |
| C3, C4 disubstituted | 20 | <2 |
| C4 | 28 | 11 |
| C5, C5+ | 16 | 50 |
| Number of quaternary branches/molecule | 0.4 | 0.3 |

Acids and anhydrides which undergo esterification with the alcohols according to the present invention can be any carboxylic acid which undergoes esterification, i.e., mono or poly-basic acids, preferably dibasic or tribasic acids, and can be aliphatic, cycloaliphatic or aromatic. They can be substituted or unsubstituted, saturated or unsaturated, or they can be blends of the aforementioned acids. Representative acids those listed in U.S. Pat. No. 6,355,711.

Preferably the acid and/or anhydride is selected from phthalic anhydride, phthalic acid, trimellitic anhydride, adipic acid, azelaic acid, benzoic acid, citric acid, oleic acid, stearic acid, terephthalic acid, and mixtures the aforementioned acids or with other acids. More preferably the acid and/or anhydride is selected from phthalic anhydride, trimellitic anhydride, adipic acid, and mixtures thereof or in combination with these and/or other acids.

The esterification process is preferably conducted in the presence of a catalyst. Typical esterification catalysts are titanium, zirconium and tin catalysts such as titanium, zirconium and tin alcoholates, carboxylates and chelates (see, for example, U.S. Pat. No. 3,056,818). Selected acid catalysts may also be used in this esterification process. Esterification processes are per se well-known, such as described in various references discussed in the Background section above.

Typically, the esterification process according to the present invention comprises (a) adding an excess of an alcohol mixture comprising at least one less branched $C_{13}$ alcohol the acid and/or anhydride in a reaction vessel, (b) heating the reaction mixture to a temperature at about or above the boiling point of the $C_{13}$ alcohol and maintaining a pressure sufficient to obtain boiling of the reaction mixture, thereby converting the acid and/or anhydride and the alcohol to the appropriate ester, e.g., in the most preferred embodiment, a phthalate, trimellitate, or adipate.

Again it is important to recognize that additional alcohols may be present in the esterification process, such as $C_{12}$ or $C_{11}$ or lower alcohols, or mixtures of alcohols, and from a cost standpoint it may even be preferred. It is preferable that these other alcohols also be less branched alcohols. It is preferred, for example the alcohol moiety in the final ester be a mixture of less branched alcohols derived from the hydroformylation of a mixture of higher olefins derived from the oligomerization of a mixture of lower olefins. It is preferred that the plasticizer ester contain at least 50%, more preferably at least 75%, still more preferably at least 90%, most preferably at least 95%, on a molar basis, of the $C_{13}$ less branched alcohol according to the present invention.

The aforementioned plasticizer ester according to the present invention, which comprises the reaction product of an acid or anhydride with a $C_{13}$ alcohol having a low number of branching and preferably wherein the branching is short chain branching, and most preferably wherein the branching is limited to methyl branching, may be mixed with other plasticizers. It may be a mixture of esters based on the $C_{13}$ alcohols according to the present invention with more than one acid, such as a mixture of trimellitate, phthalate, and adipate esters. It may be a mixture of phthalate esters having the $C_{13}$ alcohol moiety according to the present invention with TINTM or TOTM. It may also be a mixture of DTDP wherein the tridecyl moiety is a $C_{13}$ alcohol according to the present invention, with a prior art DTDP. Innumerable variations are possible.

One of the particular advantages afforded by the present invention is that it allows for less use of the more expensive trimellitate esters, and also that less oxidant need be used than might be expected (based on the teachings of the prior art as discussed previously). These and other advantages are illustrated by the following examples.

EXAMPLE

Table 3, below, sets forth the compositions used in the following examples and Table 4, further below, sets forth the results achieved.

The comparative Composition A is prepared using Jayflex™ DTDP plasticizer. The DTDP plasticizer is derived by hydroformylating an olefin obtained from a SPA unit, and has a branching number of 3.2.

Composition B, a PVC composition according to the present invention, is prepared using less branched DTDP plasticizer according to the present invention. A $C_{12}$ olefin cut having less than 2.3 methyl branches per molecule is distilled from the product prepared according to Example III of U.S. Pat. No. 4,855,527. The less branched $C_{12}$ olefin is hydroformylated and then hydrogenated in the same unit and same manner as the olefin obtained from the SPA unit, above, to obtain a less branched $C_{13}$ alcohol according to the present invention.

It is surprising that Composition B can be readily prepared to provide a useful article, given that heretofore it was believed that $C_{13}$ phthalate esters prepared from more linear $C_{13}$ alcohols were not readily compatible with PVC. Moreover, no trimellitates were used in this preparation, and yet both compositions A and B pass THHN performance tests.

Composition C illustrates another facet of this invention. While Composition A represents a typical upper limit for traditional DTDP concentrations in blends with the trimellitate plasticizer TINTM, in products designed for high temperature applications like 105° C. wire, Composition C contains 80% of the $C_{13}$ phthalate ester based on less branched alcohols according to the present invention. Although Composition B passes the retained tensile properties after accelerated aging, often in commercial practice it is desirable to add additional improvements in order to ensure the safety of the product. Composition C, with the higher phthalate concentration, which leads to advantages in lower cost, improved processability, improved low temperature flexibility, and improved plasticizer efficiency over Composition A, still has essentially the same properties as Composition A in the accelerated aging tests.

Composition D illustrates another facet of this invention. U.S. Pat. No. 4,806,425 describes wire insulation compounds for high temperature applications, that can be prepared with higher levels of branched phthalate esters provided the antioxidant Bisphenol-1 A is increased to significantly high levels. High levels of the antioxidant Topanol™ CA have similar effects when used with plasticizers such as DTDP or TINTM, TDTM, DUP and UDP. Less branched DTDP formulation of composition B needs less antioxidant to pass the accelerated aging test. Using less antioxidant in the formulation contributes to lower the cost, improved electrical resistivity, and improved color stability.

Among the remarks that can be made about the experimental results shown in Table IV, two important ones are: Composition B and C are superior to Composition A in retained elongation, without need for excess antioxidant, providing cost savings in at least one of reduced trimellitate or reduced antioxidant. Comparing B to D, B will process better than D because of less branched material, giving lower fusion temperature, B also used less $C_{13}$ phthalate giving cost savings to achieve same level of Shore A Hardness.

TABLE 3

|  | Composition A | Composition B | Composition C | Composition D |
| --- | --- | --- | --- | --- |
| PVC[1] | 100 parts | 100 parts | 100 parts | 100 parts |
| Jayflex ® TINTM | 20 | 0 | 10 | 0 |
| Jayflex ® DTDP | 30 | 0 | 0 | 47 |
| New Less Branched DTDP | 0 | 47 | 40 | 0 |
| CaCO$_3$ | 15 | 15 | 15 | 15 |
| SP-33 clay[2] | 15 | 15 | 15 | 15 |
| Lead stabilizer[3] | 6 | 6 | 6 | 6 |
| Stearic Acid | 0.25 | 0.25 | 0.25 | 0.25 |
| Sb$_2$O$_3$ | 6 | 6 | 6 | 6 |
| Antioxidant TCA (TOPANOL CA[4]) | 0.2 | 0.1 | 0.1 | 1.0% |
| Compatibility | Good | Good | Good | Good |
| Accelerated Oven Aging at 136° C. for 7 days | Pass | Pass | Pass | Marginal |

[1]PVC resin is Georgia Gulf Corporation's 5415 PVC resin
[2]The clay is Burgess Pigment Company's SP-33 clay
[3]Lead stabilizer is Bacrlocher's Dythal ®
[4]Topanol CA is 1,1,3-tris(2-methyl-4-hydroxy-5-t-butylphenyl) butane Experimental details for the results obtained below are as follows.

I. preparation of compositions—suspension PVC (a) 1. Weigh and mix formula reagents in laboratory Hobart mixer (Model N-50) at room conditions; mix all dry ingredients one minute at speed 1; add all liquids; mix 5 minutes at speed 1 at room conditions; 2. Compound into fluxed homogeneous sheet on 8"×16" equal speed; two roll mill at 28 rpm for five minutes at 166° C. (330° F.)(b) sheet off mill at—0.045' thickness; allow to cool; 3. Compression mold 6"×6" test plaques to specified thickness; using Wabash press (Model 75-184-4 STMAC):

Preheat cycle: 15 minutes at—1000 psi; 171° C. (340° F.)(b)
Mold cycle: 2 minutes at 3500 psi; 171° C. (340° F.)(b)
Cool cycle: 15 minutes with cold water on platens; 5500 psi 4. Die cut appropriate test specimens; 5. Condition test specimens under unstressed conditions for 7 days minimum at 23 11° C. (73+/−1.4° F.) 50+/−3% relative humidity.

(a) Formulations by Weight: (Suspension/Plastisol)
Geon 30 100/Geon 121 100
Plasticizer 25;35;50/50;70;90
Mark 7101 2.0/2.0
Stearic Acid 0.25—

(b) Milling and molding temperature is varied as a function of plasticizer type:
(Mill Temp./Mold Temp.)
All aliphatic acid diesters and phthalates <DIDP molecular weight
166° C. (330° F.)/71° C. (340° F.)
Jayflex UDP-D1DP range
171° C. (340° F.)/177° C. (350° F.)
All trimellitates and polyesters
117° C. (350° F.)/182° C. (360° F.)

III. Mechanical Properties (ASTM)
Durometer hardness (250 mils) D-2240
Tensile Properties (0.040") D-882
Clash-Berg; Tf (0.070") D-1043
Brittleness. Tb (0.070") D-746

IV. Permanence Properties
Oven aging; forced air 7 days at 100° C.; (0.040" thick; die cut specimens); suspend exactly 40 specimens in rack; rotating @ 6 RPM;Volatility: activated carbon; 24 hrs. at 70° C.; D-1203; Method A (0.010"×2" diameter)

Typically, the amount of antioxidant present can be about 1.5% by weight, based on the weight of the plasticizer. In an embodiment of the invention, 1.0 wt % or less, preferably 0.5 wt. % or less, still more preferably 0.1 wt. % or less of antioxidant, based on the weight of the plasticizer, is used. Specific antioxidants which may be useful include bisphenol A, Topanol CA, and Irganox 1046, and the like.

The formulation containing the polyvinyl chloride and the plasticiser according to the present invention, and optionally other plasticizers, may contain other additives. The majority of formulations will contain a stabilizer which counters the effects of aging; heat stabilizers also reduce the dehydrodehalogenation of the polyvinyl chloride at the temperatures at which the formulation is processed. Stabilizers, such as benzotriazole and benzophenone, also reduce the degradation by sunlight, ozone and biological agents. The improved ultra-violet stability obtained by the use of the esters of the cyclohexane polycarboxylic acids according to the present invention may enable smaller amounts of stabilizers to be used. Typically, the formulations contain from 0.5 to 10 parts, normally from 1.5 to 3 parts, by weight of stabilizer per 100 parts of the polyvinyl chloride.

Stabilizers to provide stability during heat processing are typically metal compounds, particularly lead salts, which are used in wire and cable applications, organotin, particularly lead salts, which are used in wire and cable applications, organotin compounds, barium, cadmin and zinc salts or calcium/zinc stabilizers. Organic phosphates and polyols may also be used. Lead stabilizers are used in wire and cable applications. Calcium/zinc stabilizer systems are used in wire and cable, foil and sheeting, wall coverings, medical applications, tubes and footwear, food packaging film and fabric coating. Barium/zinc stabilizer systems are used in foil and sheeting, flooring, wall covering, tubes and footwear and fabric coating. Tin stabilizers are used in flooring and wall covering. Zinc compounds are frequently used as a stabilizer and as a kicker in formulations used to produce foams in, for example, flooring, wall covering and fabric covering.

Other ingredients which may be added to the polyvinyl chloride formulations include fillers such as calcium carbonate, titanium dioxide or silica. When used, the filler may be present in an amount up to 75 parts per 100 parts of polyvinyl chloride. Lubricants, pigments and processing acids may be included. Other ingredients will be chosen according to the use to which the formulation is to be put. For example, the formulation may contain flame retardants, blowing agents and kickers, bio-stabilizers, antistatic agents, viscosity regulators such as thickeners and thinners, antifogging agents which are particular useful is packaging films and antioxidants, such as bisphenol A.

Fillers are incorporated in the formulations primarily to reduce cost, increase the output of dry blending, increase electrical resistance, increase resistance to ultra-violent light, increase hardness, provide improved heat transmission, and to increase the resistance to heat deformation. Fillers can also impart anti-blocking or anti-slip performance. Examples of suitable fillers include calcium carbonate, clays such as alumino-silicates, silica, dolomite and bauxite. The particular particle size distribution and average surface area of the filler will be chosen according to the properties it is desired to impart, as would be apparent to one of skill in the art.

Lubricants and processing aids may be included to reduce the adhesion between polyvinyl chloride and hot machinery surfaces during processing. The lubricants also affect the frictional properties between resin particles during processing. Examples of lubricants include stearic acid and metal stearates which can also act as stabilizers. Other lubricants that may be used include petroleum waxes, silicon oil, mineral oil, synthetic oils and polyethylene waxes.

The formulations may also contain flame retardants to increase ignition time, reduce flame spreading and rate of burning. The flame retardants should have a high decomposition temperature, low volatility, a minimum effect on thermal and mechanical properties and good resistance to light and ultra-violet radiation. Examples of flame retardants that may be used include halogen containing compounds and phosphorous containing organic compounds such as triaryl, trialkyl or alkyl diaryl phosphate esters. Other materials that may be used include chloroparaffins, aluminum trihydrate $Al(OH)_3$ or antimony oxides $Sb_2O_3$.

TABLE 4

PERFORMANCE OF DTDP COMPOUNDS

| Physical Properties | Composition A | Composition B | Composition C | Composition D |
|---|---|---|---|---|
| Shore A Hardness | 90.5 | 90.5 | 90.5 | 92 |
| Shore D Hardness | 42.5 | 43.0 | 42.8 | 44 |
| 100% Modulus (N/mm^2) | 14 | 14 | 13 | 13 |
| Tensile Strength (N/mm^2) | 20 | 20 | 20 | 20 |
| Elongation, % | 278 | 266 | 280 | 260 |
| Clash - Berg (Tf), ° C. | −18.4 | −19 | −19.8 | −18 |
| Brittleness (Tb), ° C. | −21.5 | −22 | −22.2 | −20 |
| Retained Tensile (%), 136° C., 7 days | 110 | 110 | 99 | 106 |
| Retained Elongation (%), 136° C., 7 days | 75 | 77 | 85 | 70 |
| Weight Loss (%), 100° C., 7 days | 0.9 | 1.0 | 0.9 | 1.2 |
| Volatility Carbon Black, Wt. Loss, 24 hr., 70° C. | 0.5 | 0.4 | 0.5 | 0.4 |
| Compound Specific Gravity | 1.3578 | 1.3616 | 1.3550 | 1.3522 |

Trade names used herein are indicated by a ™ symbol or ® symbol, indicating that the names may be protected by certain trademark rights, e.g., they may be registered trademarks in various jurisdictions.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims.

What is claimed is:

1. A composition comprising a plasticizer ester prepared by esterifying an ester precursor selected from the group consisting of at least one acid, at least one anhydride, and a mixture thereof, with a less branched $C_{13}$ alcohol molecule having an average of from 0.5 to 2.0 branches per alcohol molecule.

2. The plasticizer ester according to claim 1, wherein said ester precursor is selected from the group consisting of adipic acid, phthalic anhydride, trimellitic anhydride, and mixtures thereof.

3. The plasticizer ester according to claim 1, wherein said ester precursor is phthalic anhydride.

4. The plasticizer ester according to claim 1, wherein in the $^1$H NMR spectrum of said ester, measured in the solvent $CDC_{13}$, the ratio of integrated area of the resonance signals with chemical shifts in the range from 1.1 to 3.0 ppm to the integrated area of the resonance signals with chemical shifts in the range of 0.5 to 1.1 ppm is between about 1.20 and about 3.50 ppm, the chemical shift in ppm measured relative to the internal standard TMS.

5. The plasticizer ester according to claim 4, wherein said ratio is between about 2.40 to about 3.50 ppm.

6. The plasticizer ester according to claim 1, prepared by esterifying said ester precursor with a less branched $C_{13}$ alcohol having an average of 0.5 to 2.0 branches per alcohol.

7. The composition according to claim 1, prepared by esterifying said ester precursor with a less branched $C_{13}$ alcohol having an average of 0.8 to 1.5 branches per alcohol.

8. The composition according to claim 1, further having a branching index of less than 20.

9. The composition according to claim 1, further comprising PVC.

10. The composition according to claim 1, further comprising esters having as the alcohol moiety less branched $C_{11}$ and $C_{12}$ alcohols.

11. The composition according to claim 1, further comprising esters selected from the group consisting of TOTM, TINTM, and mixtures thereof.

12. A composition comprising a resin and a plasticizer, said plasticizer comprising a plasticizing ester prepared by esterifying at least one ester precursor selected from the group consisting of phthalic acid, phthalic anhydride, and mixtures thereof, with a less branched $C_{13}$ alcohol having an average of from 0.5 to 2.0 or less branches per alcohol molecule.

13. The composition according to claim 12, wherein said plasticizer further comprises trimellitate esters.

14. The composition according to claim 13, wherein said plasticizing ester prepared by esterifying at least one ester precursor selected from the group consisting of phthalic acid, phthalic anhydride, and mixtures thereof, comprises greater than 60 wt. % of the total plasticizer.

15. The composition according to claim 13, wherein said plasticizing ester prepared by esterifying at least one ester precursor selected from the group consisting of phthalic acid, phthalic anhydride, and mixtures thereof, with a less branched $C_{13}$ alcohol having an average of from 0.5 to 2.0 or less branches per alcohol comprises greater than 70 wt. % of the total plasticizer.

16. The composition according to claim 12, further comprising fillers selected from the group consisting of calcium carbonate, calcined clay, and mixtures thereof.

17. The composition according to claim 12, further comprising at least one stabilizer selected from the group consisting of mixed metal salts of calcium, mixed metal salts of zinc, and lead-based stabilizers.

18. An article comprising the resin composition of claim 12.

19. The article according to claim 18, wherein said article is a flexible PVC electrical insulation product meeting the requirements of at least one of the standards set by THHN 90° C., NM-B 90° C., UL 12, UL 758, or 105° C. designations according to VDE Specification Code 0207.

20. The composition according to claim 1, said composition further characterized by having 1.0 wt % or less antioxidant, based on the weight of the plasticizer.

21. The composition according to claim 12, said composition further characterized by having 1.0 wt % or less antioxidant, based on the weight of the plasticizer.

22. The composition according to claim 1, said composition further characterized by having an average of from 0.8 to 1.5 branches per alcohol molecule.

23. The composition according to claim 12, said composition further characterized by having an average of from 0.8 to 1.5 branches per alcohol molecule.

24. The composition according to claim 1, said composition further characterized by having 0.5 wt % or less antioxidant, based on the weight of the plasticizer.

25. The composition according to claim 12, said composition further characterized by having 0.5 wt % or less antioxidant, based on the weight of the plasticizer.

* * * * *